United States Patent
Miyoshi et al.

(10) Patent No.: US 7,257,997 B2
(45) Date of Patent: Aug. 21, 2007

(54) METHOD OF DETECTING LONGITUDINAL FORCE OF TIRE AND LONGITUDINAL FORCE DETECTING APPARATUS USED THEREIN

(75) Inventors: Akihiro Miyoshi, Kobe (JP); Keita Nakano, Kariya (JP)

(73) Assignees: Sumitomo Rubber Industries, Ltd., Kobe-shi, Hyogo-ken (JP); Advics Co., Ltd., Kariya-shi, Aichi-ken (JP)

( * ) Notice: Subject to any disclaimer, the term of this patent is extended or adjusted under 35 U.S.C. 154(b) by 0 days.

(21) Appl. No.: 11/392,704

(22) Filed: Mar. 30, 2006

(65) Prior Publication Data

US 2006/0219000 A1  Oct. 5, 2006

(30) Foreign Application Priority Data

Mar. 31, 2005 (JP) .............................. 2005-103052

(51) Int. Cl.
*G01M 17/02* (2006.01)
(52) U.S. Cl. ......................... 73/146; 340/445
(58) Field of Classification Search ................. 73/146; 340/445

See application file for complete search history.

(56) References Cited

U.S. PATENT DOCUMENTS 6,339,956 B1 * 1/2002 Huinink et al. ............... 73/146
6,959,592 B2 * 11/2005 Caretta ........................ 73/146
6,959,593 B2 * 11/2005 Mancosu et al. ............. 73/146

FOREIGN PATENT DOCUMENTS

WO  WO-96/10505 A1  4/1996

* cited by examiner

*Primary Examiner*—Andre J. Allen
(74) *Attorney, Agent, or Firm*—Birch, Stewart, Kolasch and Birch, LLP

(57) ABSTRACT

An apparatus for detecting a longitudinal force of a tire is provided with at least one mark (3) provided in on one circumferential line (j) in a tire (2), a first sensor (5) disposed in a vehicle body side (4) and capable of detecting a passage of the mark (3), a second sensor (7) capable of detecting a rotation angle ($\theta$) of an axle (6), and a computing device (8) for computing a longitudinal force (Fr) of the tire (2) on the basis of an information of the first and second sensors (5, 7). The computing device (8) sequentially stores a rotation angle ($\theta r$) of the axle (6) when the mark (3) passes through the first sensor (5). Further, the computing device (8) computes a tire warp angle ($\alpha r$) corresponding to a difference ($\theta o - \theta r$) between a no-load rotation angle $\theta o$ (a rotation angle of the axle (6) in a no-load state) stored in advance and the rotation angle $\theta r$, and sequentially computes a tire longitudinal force (Fr) of a tire applied during the running from the warp angle ($\alpha r$), using a previously determined relational equation $F=f(\alpha)$ between the warp angle ($\alpha$) and the tire longitudinal force (F).

10 Claims, 6 Drawing Sheets

METHOD OF DETECTING LONGITUDINAL FORCE OF TIRE AND LONGITUDINAL FORCE DETECTING APPARATUS USED THEREIN

BACKGROUND OF THE INVENTION

1. Field of the Invention

The present invention relates to a method of detecting a longitudinal force of a tire which can detect a longitudinal force (a force in a tire circumferential direction) applied to the tire at a high precision on the basis of a warp angle of the tire, can accurately comprehend a rolling condition of the tire, and can make a contribution to a control of a vehicle control system, and a longitudinal force detecting apparatus used therein.

2. Description of the Related Art

In recent years, in order to secure a stability and a safety of a running motor vehicle, there has been developed various vehicle control systems such as an antilock brake system (ABS), a traction control system (TCS), an electric stability control (ESC) and the like. Further, in order to control these systems, it is necessary to accurately comprehend a rolling condition of the running tire.

For example, in the ABS, it is important to maintain a rolling state having a road surface friction coefficient as large as possible, and the road surface friction coefficient depends on a slip rate of a wheel under a fixed road surface state. Accordingly, the conventional ABS measures a speed of the vehicle and a rotating speed of the wheel, estimates the slip rate on the basis of the measured speed and rotating speed, and controls a lock/unlock of the tire in such a manner that the slip rate is maintained in a range near a position at which the road surface friction coefficient becomes maximum. In this case, on the assumption that a moving speed of the vehicle body of the motor vehicle is set to a vehicle body speed V1, and the speed of the motor vehicle specified by the rotating speed of the wheel (the tire) is set to a wheel speed V2, the slip rate can be expressed by the following expression.

$$\{(V1-V2)/V1\} \times 100(\%)$$

Further, the slip rate 100% means a state in which the wheel speed V2 equals to zero, that is, a state in which the wheel (the tire) slips while being completely locked.

However, since the road surface friction coefficient changes hour by hour in correspondence to the road surface condition, a relation between the road surface friction coefficient and the slip rate is not necessarily fixed. Accordingly, in the lock/unlock control of the tire on the basis of the slip rate, there is a risk that a problem the road surface friction coefficient becomes small is generated, even in the case that the slip rate is maintained in a predetermined range.

In order to correspond to the problem mentioned above, in recent years, there has been proposed a structure which measures a longitudinal force (a force in a circumferential direction) applied to the tire, and determining the road surface friction coefficient on the basis of the measured longitudinal force. Further, as a method of measuring the longitudinal force, the structure in Japanese National Publication of International Patent Application No. 10-506346 (corresponding to International Publication No. WO96/10505) has been known.

In the Japanese National Publication of International Patent Application No. 10-506346 (corresponding to International Publication No. WO96/10505), two reference points are provided on one radial line in a side wall surface, and a magnetic body is arranged in each of the reference points. Further, a magnetic sensor is fixed to two positions opposing to the respective reference points. Further, two magnetic sensors measure a relative temporal shift amount at a time of detecting passage of each of the magnetic bodies. Since the temporal shift amount is in proportion to a warp deformation amount of the tire, it is possible to determine the longitudinal force applied to the tire on the basis of the temporal shift amount.

SUMMARY OF THE INVENTION

However, in recent years, a flattening of the tire is promoted mainly for improving a steering stability. Accordingly, it becomes hard dimensionally in a flat tire having a narrow width of a region of a side wall portion, to form the magnetic bodies at two inner and outer positions in a radial direction of the sidewall portion, as in the method of the Japanese National Publication of International Patent Application No. 10-506346 (corresponding to International Publication No. WO96/10505) mentioned above. Further, since a distance in the radial direction between the magnetic bodies becomes small, a gain of the temporal shift amount is small, and since both the reference positions are affected by the warp deformation of the tire, it is hard to sufficiently increase a measuring precision.

Accordingly, an object of the present invention is to provide a method of detecting a longitudinal force of a tire which can detect the longitudinal force applied to the tire while having a simple structure, and having a high reliability and precision even in a flat tire, and a longitudinal force detecting apparatus of the tire used therein.

In order to achieve the object mentioned above, in accordance with a first aspect of the present invention, there is provide a method of detecting a longitudinal force of a tire which detects the longitudinal force in a circumferential direction applied to the tire, comprising:

at least one mark provided in the tire on one circumferential line around a tire axis;

a first sensor fixed to a vehicle body and capable of sequentially detecting a passage of the mark rotating together with the tire;

a second sensor capable of detecting a rotation angle $\theta$ of an axle; and a computing means for computing a longitudinal force applied to the tire on the basis of an information from the first and second sensors, wherein the computing means comprises:

(1) sequentially storing an information of a rotation angle $\theta r$ of the axle detected by the second sensor when receiving information of the passage signal from the first sensor according to the passage of the mark;

(2) previously storing an information of a no-load rotation angle $\theta o$ of the axle detected by the second sensor when receiving information of the passage signal from the first sensor according to the passage of the mark as the tire rotates in a no-load state;

(3) sequentially computing a tire warp angle $\alpha r$ corresponding to a difference ($\theta o - \theta r$) between the rotation angle $\theta r$ and the no-load rotation angle $\theta o$; and (4) sequentially computing a longitudinal force Fr of a tire applied during the running from the warp angle $\alpha r$ using a previously determined relational equation between the tire warp angle $\alpha$ and the longitudinal force F applied to the tire.

Further, in accordance with a second aspect of the present invention, there is provided an apparatus for detecting a longitudinal force of a tire which detects the longitudinal force in a circumferential direction applied to the tire, comprising:

at least one mark provided in the tire on one circumferential line around a tire axis;

a first sensor fixed to a vehicle body and capable of sequentially detecting a passage of the mark rotating together with the tire;

a second sensor capable of detecting a rotation angle $\theta$ of an axle; and a computing means for computing a longitudinal force applied to the tire on the basis of information from the first and second sensors, wherein the computing means comprises:

a rotation angle information memory portion sequentially storing information of a rotation angle $\theta r$ of the axle detected by the second sensor when receiving information of the passage signal from the first sensor according to the passage of the mark;

a no-load rotation angle information memory portion storing an information of a no-load rotation angle $\theta o$ of the axle detected by the second sensor when receiving information of the passage signal from the first sensor generated on the basis of the passage of the mark as the tire rotates in a no-load state;

a first computing portion sequentially computing a tire warp angle $\alpha r$ corresponding to a difference $(\theta o - \theta r)$ between the rotation angle $\theta r$ of the rotation angle information memory portion and the no-load rotation angle $\theta o$ of the no-load rotation angle information memory portion; and a second computing portion sequentially computing a longitudinal force Fr of a rolling tire from the warp angle $\alpha r$ computed by the first computing portion, using a previously determined relational equation between the tire warp angle $\alpha$ and the longitudinal force F applied to the tire.

Effect of the Invention

In accordance with the present invention, at least one mark is formed in the tire, and the first sensor capable of sequentially detecting the passage of the mark with the tire rotation is attached to the vehicle body side. Further, the second sensor detects the rotation angle $\theta r$ of the axle at a time when the first sensor detects the passage of the mark. Further, the rotation angle $\theta r$ of the axle is compared with the no-load rotation angle $\theta o$, that is, a rotation angle $\theta o$ of the axle when the tire rotates in the no-load state which has been previously stored in the computing means, and the tire warp angle $\alpha r$ corresponding to the difference $(\theta o - \theta r)$ is sequentially computed. Accordingly, it is possible to sequentially compute the longitudinal force Fr of the tire applied during the running, from the warp angle $\alpha r$, by using the previously determined relational equation between the tire warp angle $\alpha$ and the longitudinal force F of the tire.

As mentioned above, the present invention is structured such as to detect the rotation angle of the axle and directly determine the tire warp angle $\alpha r$ itself. Accordingly, the structure becomes simple. Further, the computing process can be easily executed in comparison with the case of using the relative temporal shift amount, and it is possible to determine the longitudinal force Fr of the tire at an excellent computing precision and an excellent processing speed.

Further, since the mark is formed on one circumferential line, it is possible to employ even in the flat tire having the narrow width of the region of the side wall portion. Further, since the great gain can be obtained, and the detected rotation angle $\theta$ of the axle can be obtained not as a relative value but as an absolute position data, it is possible to obtain the longitudinal force Fr of the tire at a higher precision and a higher reliability. In this case, the second sensor can be used as an existing rotation speed sensor and an existing rotation acceleration sensor (may be referred to as a "rotation sensor") for the ABS. Accordingly, it is possible to suppress an increase of a number of sensors, and to contribute to a cost saving as an entire of the apparatus and a simplification of the structure.

In this case, the detecting method of the longitudinal force Fr achieved by measuring the rotation angle $\theta r$ of the axle can be devised on the basis of an appearance of a high-performance angle sensor having a resolving power equal to or less than 0.10 degree in recent years, and can be carried out.

BEST MODE FOR CARRYING OUT THE INVENTION

A description will be given below of an embodiment in accordance with the present invention together with an illustrated example.

Figure 1:
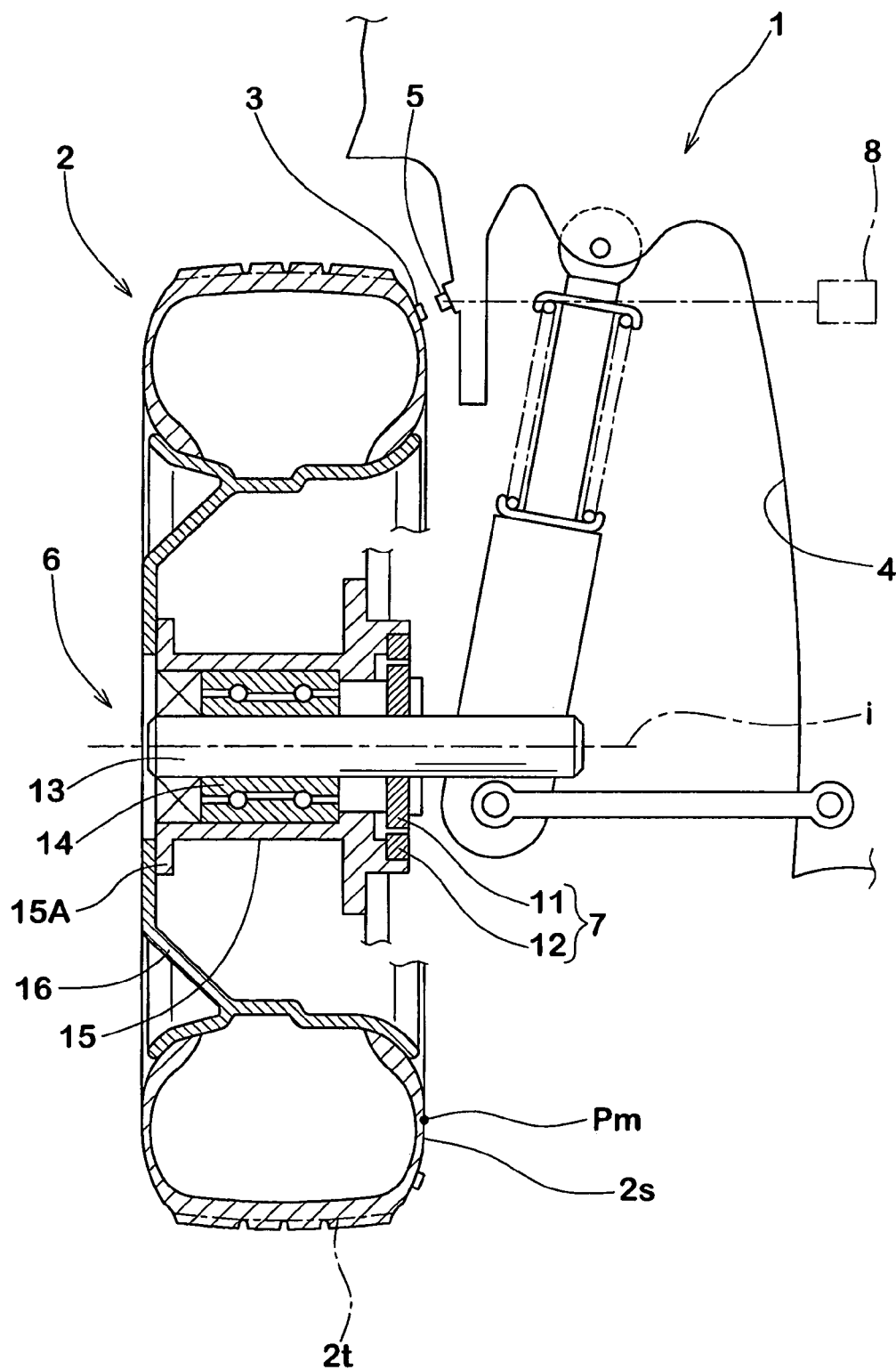
FIG. 1 is a cross sectional view showing an example of a longitudinal force detecting apparatus of a tire in accordance with the present invention together with an axle.
Figure 2:
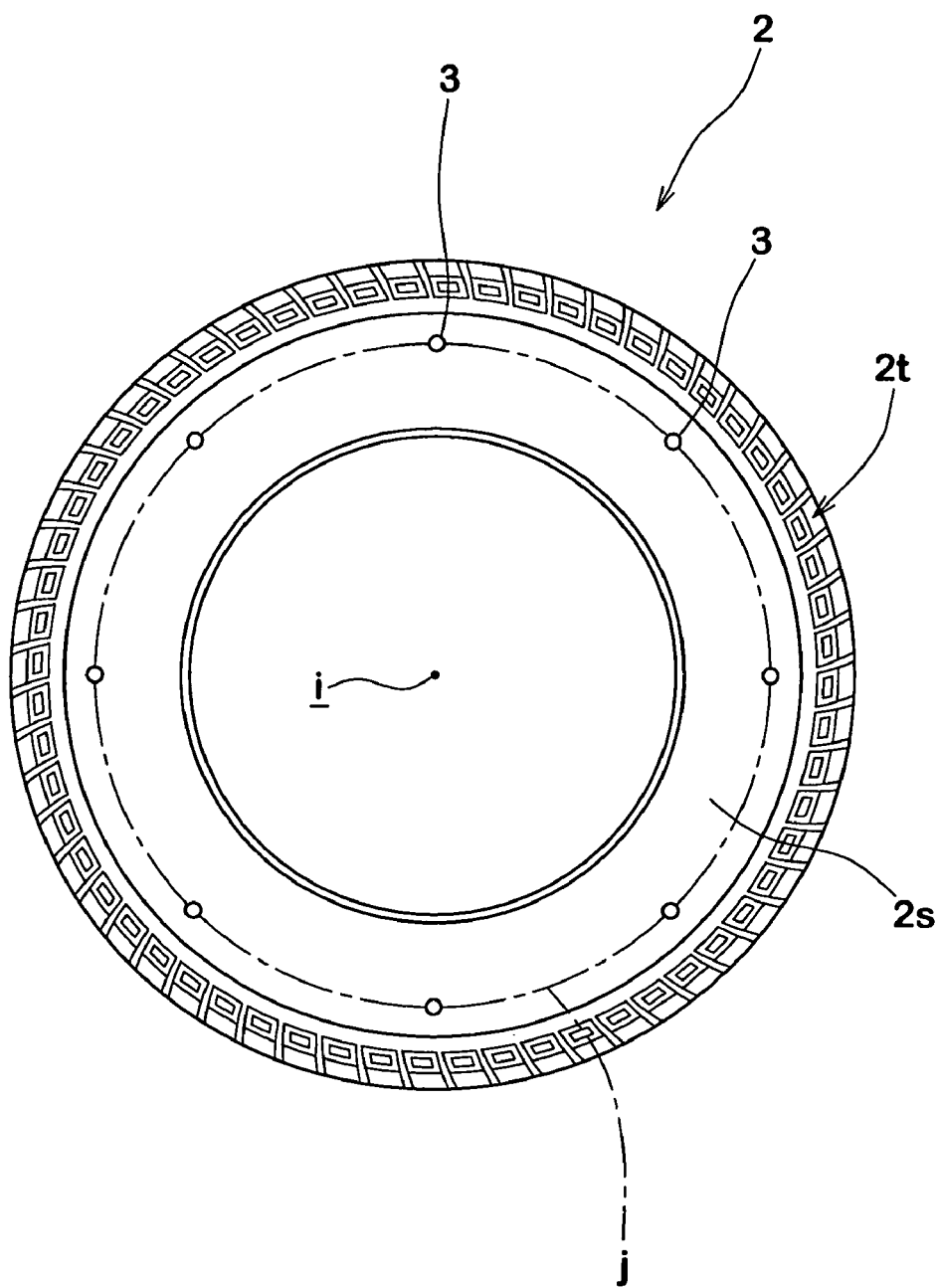
FIG. 2 is a side elevational view of the tire as seen from an inner side of a vehicle body.

FIG. 1 is a cross sectional view showing a longitudinal force detecting apparatus of a tire in accordance with the present invention together with an axle, and FIG. 2 is a side elevational view of the tire as seen from an inner side of a vehicle body.

As shown in FIG. 1, a longitudinal force detecting apparatus 1 of the tire in accordance with the present embodiment is structured such as to include:

at least one mark 3 provided in the tire 2 on one circumferential line j (shown in FIG. 2) around a tire axis i;

a first sensor 5 fixed to a vehicle body 4 and capable of sequentially detecting a passage of each mark 3 rotating together with the tire 2;

a second sensor 7 capable of detecting a rotation angle $\theta$ of an axle 6; and a computing means 8 for computing a longitudinal force Fr applied to the tire 2 on the basis of an information from the first and second sensors 5 and 7.

The mark 3 is a detected body of the first sensor 5, and is appropriately selected in accordance with a kind of the first sensor 5. For example, the present embodiment exemplifies a case that the first sensor 5 is a light reflection optical sensor, and the mark 3 is a reflecting plate reflecting the sensor light from the optical sensor. In this case, the optical sensor detects a light intensity change of the reflected light generated when the reflecting plate (the mark 3) passes below the optical sensor (the first sensor 5), whereby it is possible to sequentially detect the passage of the mark 3.

As the reflecting plate, it is possible to include a seal attached to the tire 2, and a printed body such as an ink or the like which is directly applied to the tire 2. Further, various combinations may be employed as a combination of the first sensor 5 and the mark 3, for example, a combination of a magnetic body (the mark 3) and a magnetic sensor (the first sensor 5) detecting a magnetic change, a combination of a concavo-convex portion (the mark 3) and a magnetic mutation sensor (the first sensor 5) detecting the concavo-convexportion, a combination of the concavo-convex portion (the mark 3) and an ultrasonic sensor (the first sensor 5) detecting the concavo-convex portion, and the like.

Further, it is preferable that the mark 3 is provided in a side wall portion 2s, particularly in view of making a warp deformation amount of the tire large and increasing a measuring precision, the mark is desirably provided in an outer side wall region which is outside in a radial direction from a tire maximum width position Pm. In this case, the side wall portion 2s means a region from an outer end in a tire axial direction to a rim apart position where the tire is apart from a rim flange of a tread pattern 2t, in the present specification. Further, a number of the marks 3 is preferably in a range between 4 and 72 and formed on the circumferential line j at an equal interval. If the forming number is less than 4, a detecting frequency of the longitudinal force Fr becomes excessively small, and a response speed of the vehicle control system such as the ABS or the like is insufficient. If the number is more than 72, the detecting frequency becomes excessively large, and an unnecessary cost increase is caused such that a high-performance microprocessor having a high computing processing performance is necessary, or the like.

Further, the first sensor 5 is attached to the vehicle body 4 at a position to detect the passage of the mark 3.

Next, the second sensor 7 is a rotation angle sensor such as a so-called resolver, encoder or the like, to detect a rotation angle $\theta$ of the axle 6 and measures the rotation angle $\theta$ of the axle 6 from a reference point Po (shown in FIG. 3), that is, an absolute angular position, at least within one rotation. Preferably, a multi rotation type sensor which can measure the rotation speed of the axle 6 is employed in view of saving a cost of an entire apparatus and simplifying the structure, since it can be used as a rotation sensor at the same time.

In the present embodiment, there is exemplified a structure in which the resolver is used as the second sensor 7. The resolver has a well-know structure including a rotor 11 and a stator 12. The axle 6 includes an axle main body 13 supported to the vehicle body 4, and an outer tube member 15 rotatably held to the axle main body 13 via a bearing member 14. The outer tube member 15 is structured such that a tire wheel 16 is fastened by bolt to a flange 15A provided in a front end thereof. Further, the rotor 11 is fixed to the axle main body 13, and the stator 12 outside inserted so as to be relatively rotatable with the rotor 11 is fixed to the outer tube member 15.

In the case of the running tire, the axle main body 13 is rotationally driven, and the tire wheel 16 is fastened by bolt to a front end thereof. At this time, the outer tube member 15 is supported to the vehicle body 4, and rotatably holds the rotationally driven axle main body 13 via the bearing member 14. In the case mentioned above, it is possible to detect the rotation angle $\theta$ of the axle 6 by fixing the rotor 11 to the axle main body 13 and fixing the stator 12 to the outer tube member 15.

Figure 3A:
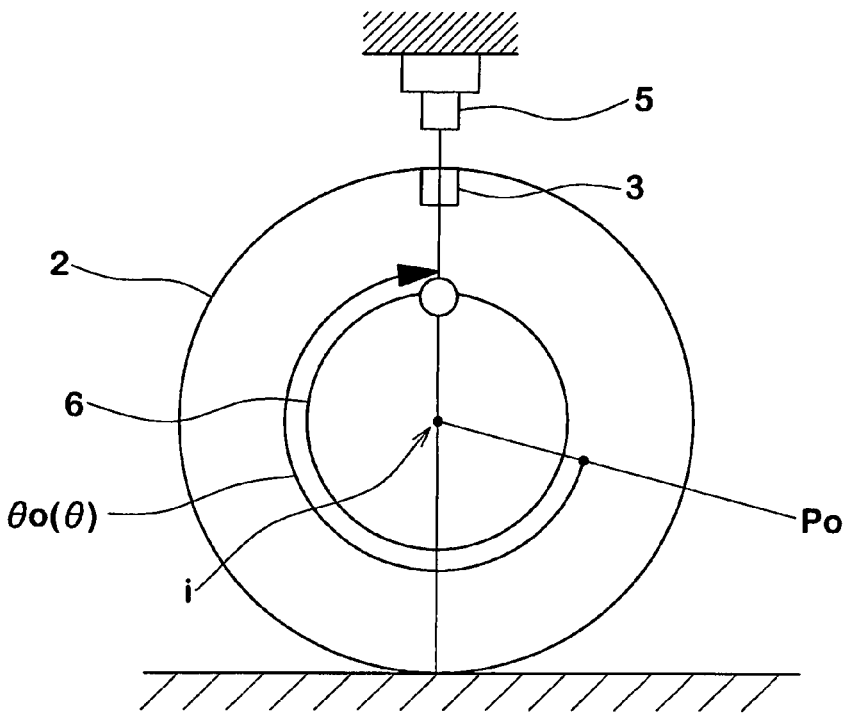
FIG. 3(A) is a view explaining a rotation angle of the axle when the tire rotates in a no-load state.

When the tire rotates in a no-load state, the rotation angle $\theta$ of the axle 6 at a time when the mark 3 passes through the first sensor 5 becomes a no-load rotation angle $\theta o$ having no warp deformation, as shown in FIG. 3(A). In this case, the rotation angle $\theta$ corresponds to an absolute angle from the reference point Po, and the reference point Po can be freely set in accordance with the second sensor 7.

Figure 3B:
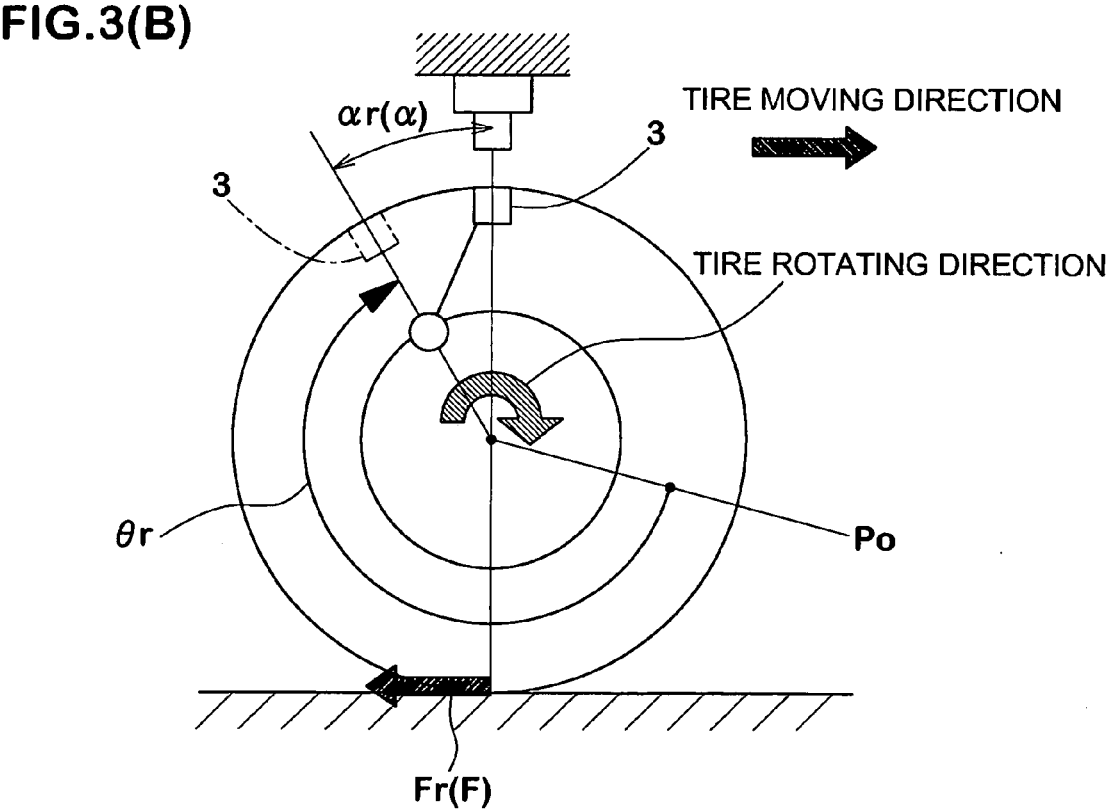
FIG. 3(B) is a view explaining the rotation angle of the axle when a longitudinal force is applied to the tire.

On the contrary, in the case that the longitudinal force F is applied by braking the tire 2, the warp deformation is generated in the tire 2 in the rotating direction by the longitudinal force Fr, as shown in FIG. 3(B). In other words, a phase of the mark 3 is shifted to the rotating direction side with respect to the axle 6. Accordingly, the rotation angle $\theta r$ of the axle 6 when the mark 3 passes through the first sensor 5 becomes smaller in comparison with the no-load rotation angle $\theta o$, and a difference ($\theta o - \theta r$) at that time corresponds to a warp angle $\alpha r$ of the tire caused by the longitudinal force F.

Next, a correlation exists between the warp angle $\alpha$ and the longitudinal force F, and it is possible to determine the longitudinal force Fr applied at that time, on the basis of the warp angle $\alpha r$, by using a relational equation ($F=f(\alpha)$). In general, it can be approximated by the following relational equation.

$$F = K \times \alpha \tag{1}$$

The coefficient K is a longitudinal spring constant specific for the tire, and can be determined on the basis of a tire individual experimental value obtained by previously measuring the relation between the warp angle $\alpha$ and the longitudinal force F. The relational equation is not limited to the equation (1) mentioned above, but may be constituted by a complicated relational equation, for example, determined by an experiment while taking the tire rotation speed, the internal pressure or the like into consideration.

Further, in accordance with the present invention, the longitudinal force Fr is computed by using the computing means 8.

Figure 4:
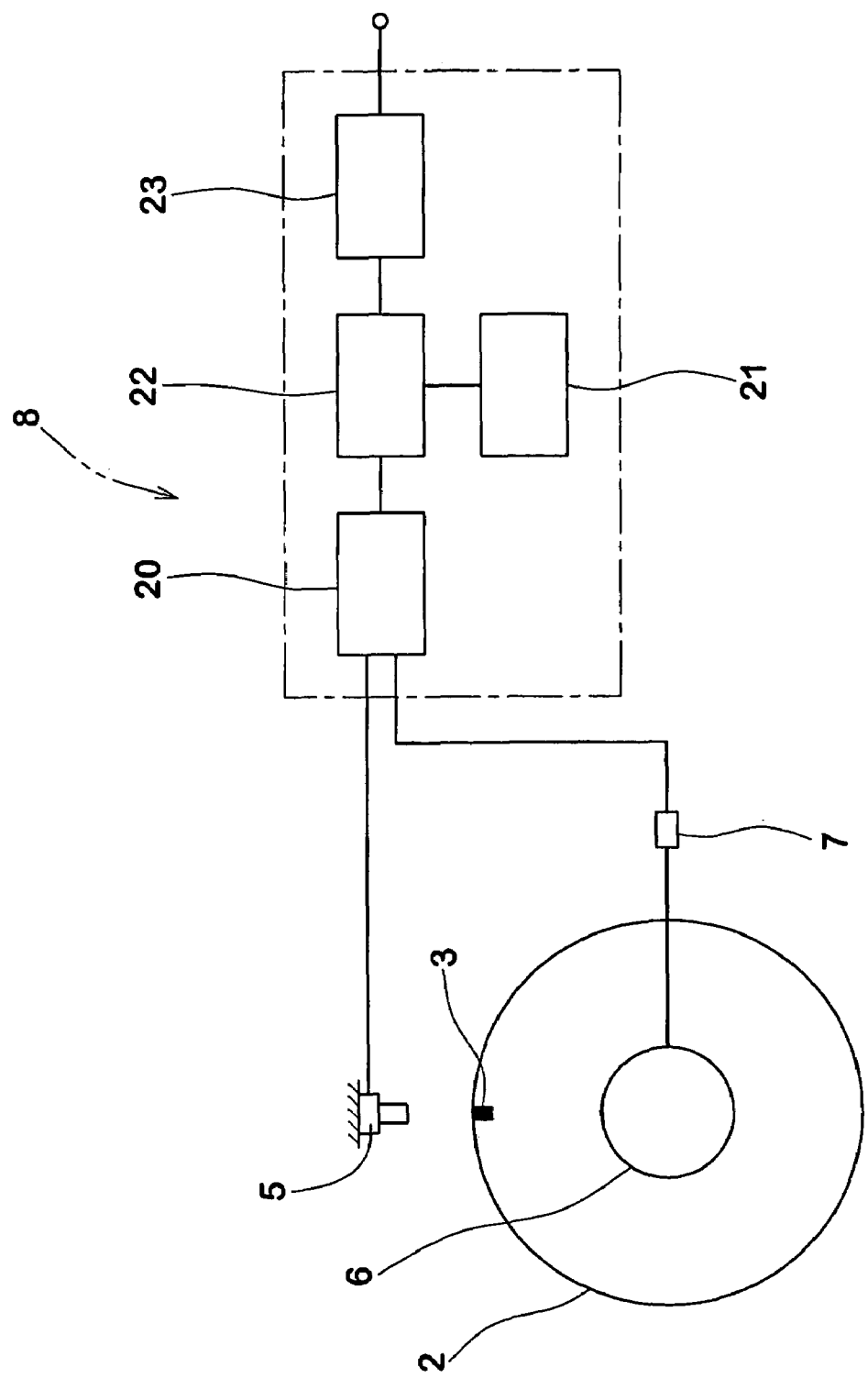
FIG. 4 is a view explaining a computing means.

The computing means 8 is structured, as shown in FIG. 4, such as to include a rotation angle information memory portion 20, a no-load rotation angle information memory portion 21, a first computing portion 22, and a second computing portion 23. The rotation angle information memory portion 20 sequentially stores the information of the rotation angle $\theta r$ of the axle 6 detected by the second sensor 7 when receiving the information of the passage signal from the first sensor 5 according to the passage of the mark 3. In this case, the second sensor 7 continuously outputs the information of the rotation angle $\theta$ of the axle 6, while the first sensor 5 detects an instant when the mark 3 passes through the first sensor 5 and outputs the information of the passage signal to the computing means 8. Further, the rotation angle information memory portion 20 sequentially stores the information of the rotation angle $\theta r$ when receiving the information of the passage signal. The rotation angle $\theta r$ at this time corresponds to an angle including the warp angle $\alpha r$ of the tire caused by the longitudinal force Fr.

Further, in the case that the tire rotates in the no-load state, the no-load rotation angle information memory portion 21 previously stores the information of the no-load rotation angle $\theta o$ of the axle 6 detected by the second sensor 7 when receiving the information of the passage signal from the first sensor 5 generated on the basis of the passage of the mark 3. The information of the no-load rotation angle $\theta o$ can be stored in advance, for example, when conducting a vehicle inspection, in the no-load rotation angle information memory portion 21.

The first computing portion 22 calls the stored rotation angle $\theta r$ and the no-load rotation angle $\theta o$, and sequentially computes the warp angle $\alpha r$ of the tire corresponding to the difference ($\theta o - \theta r$) thereof.

Further, the second computing portion 23 sequentially computes the longitudinal force Fr applied to the tire, from the warp angle $\alpha r$ computed by the first computing portion 22, on the basis of the relational equation (F=f(α)). In this case, the relational equation (F=f(α)) between the warp angle α and the longitudinal force F can be previously determined, for example, in an inspection at a time of manufacturing the tire.

In this case, if a resolving power of the second sensor 7 is larger than 0.10 degree, a resolving power of the longitudinal force Fr determined by the computing means 8 also become larger than 750 N, as shown in a test result in Table 1 mentioned below, so that it is substantially hard to effectively apply to the vehicle control system such as ABS, TCS, ESC or the like. Accordingly, it is necessary that the resolving power of the second sensor 7 is not more than 0.10 degree, preferably not more than 0.05 degree.

Further, in the second computing portion 23, a direction of the longitudinal force Fr is computed according to positive or negative of the difference (θo−θr): When the difference (θo−θr) is positive, the longitudinal force Fr is detected as the braking force, and when it is negative, the longitudinal force Fr is detected as the driving force.

Figure 5:
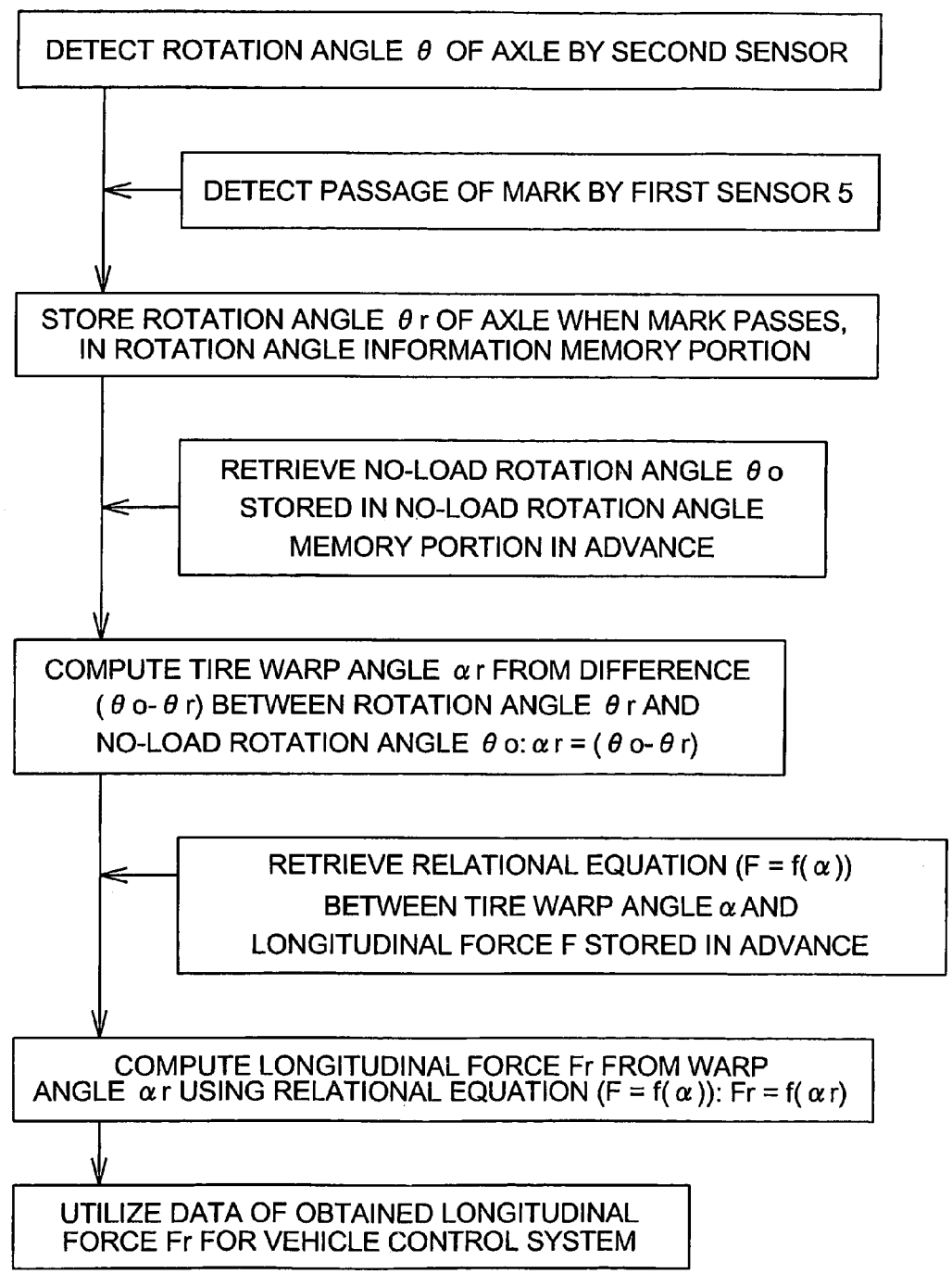
FIG. 5 is a flow chart explaining a longitudinal force detecting method.

FIG. 5 is a flow chart of a longitudinal force detecting method executed by using the detecting apparatus 1.

In FIG. 5, in the longitudinal force detecting method, first, the rotation angle θ of the axle 6 is continuously detected by the second sensor 7, and the information of the rotation angle θ is output to the computing means 8. Further, the first sensor 5 sequentially detects the instant when the mark 3 passes through the first sensor 5, and outputs the information of the passage signal to the computing means 8.

The computing means 8 sequentially stores, among the information of the rotation angle θ output as above, the information of the rotation angle θr when receiving the information of the passage signal in the rotation angle information memory portion 20. Further, the first computing portion 22 compares the information of the rotation angle θr with the information of the no-load rotation angle θo stored in the no-load rotation angle information memory portion 21 in advance, and sequentially computes the warp angle αr of the tire corresponding to the difference (θo−θr) thereof. Thereafter, the longitudinal force Fr applied to the tire is sequentially computed by the second computing portion 23 from the warp angle αr by using the previously determined relational equation (F=f(α)).

Further, the longitudinal force Fr obtained as above is sequentially output to the vehicle control system such as ABS, TCS, ESC or the like, and is effectively utilized for the system.

As mentioned above, since the structure is made such as to detect the rotation angle θ of the axle 6 and directly determine the warp angle αr of the tire 2, the structure is simple, and the computing process can be easily executed in comparison with the case of the computing process via the relative temporal shift amount. As a result, it is possible to obtain the longitudinal force Fr of the tire at a higher computing precision and an excellent processing speed. Further, since the mark is provided on the same circumferential line, it is possible to easily employ the structure in any kind of tire, even in the flat tire. Further, since a great gain can be obtained, and the detected rotation angle θ of the axle can be obtained not as a relative value, but as an absolute position data, it is possible to obtain the longitudinal force Fr of the tire 2 at a higher precision and a higher reliability. Further, since the second sensor 7 can be used as a rotation speed sensor for the ABS, it is possible to suppress an increase of a number of sensors, and to contribute to a cost saving as an entire of the apparatus and a simplification of the structure.

The description is in detail given above of the particularly preferable embodiment in accordance with the present invention, however, the present invention is not limited to the illustrated embodiment, but can be carried out by modifying into various aspects.

EXAMPLE

By using the detecting method in accordance with the present invention, the longitudinal force applied to the tire was detected on the basis of the specification in Table 1, and a resolving power of the detection and an effectiveness to the vehicle control system such as ABS, TCS, ESC or the like are evaluated by four stages comprising x, Δ, ○ and ◉. In this case, the sign Δ means the same level as the performance in the current vehicle control system.

Figure 6A:
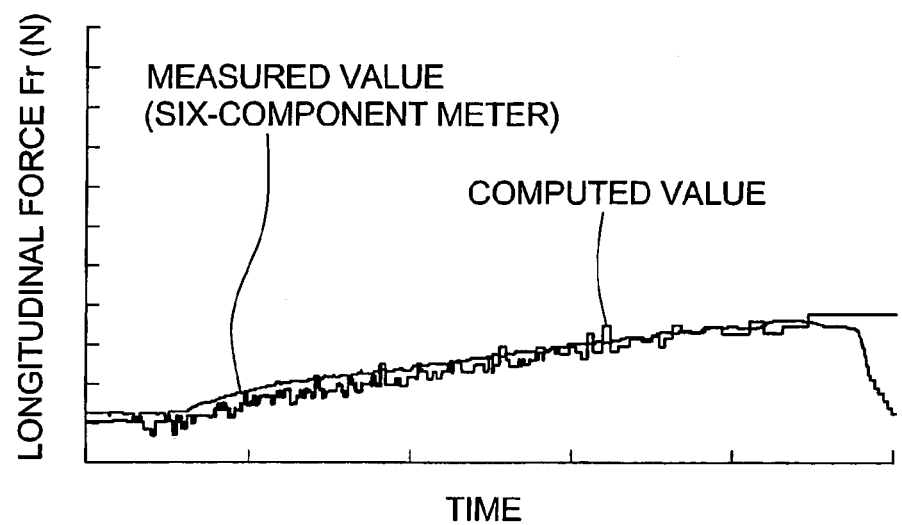
FIGS. 6(A) and 6(B) are graphs showing a result obtained by detecting the longitudinal force applied to the tire when braking, by using the longitudinal force detecting method in accordance with the present invention.
Figure 6B:
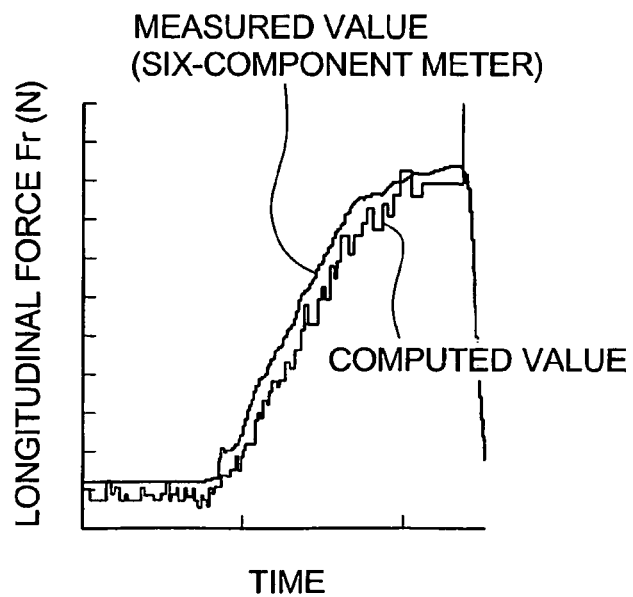

Further, the tire was attached to the vehicle and the vehicle was run actually, and the longitudinal force generated in the tire at that time was compared between a case that the longitudinal force was detected on the basis of the specification in the example 2, and a case that the longitudinal force was measured by using a six-component meter. The result of comparison is shown in FIGS. 6(A) and 6(B). FIG. 6A shows a case of slowly putting on the brake from a constant speed running state at a speed of 40 km/h, that is, a case that a small longitudinal force was applied. Further, FIG. 6(B) shows a case of braking hard during the constant speed running state at the speed of 40 km/h, that is, a case that a large longitudinal force was applied.

TABLE 1

|  | Comparative Example 1 | Comparative Example 2 | Example 1 | Example 2 | Example 3 | Example 4 |
| --- | --- | --- | --- | --- | --- | --- |
| Forming number of mark | 1 | 8 | 8 | 8 | 8 | 32 |
| Resolving power of second sensor | 1 degree | 1 degree | 0.1 degree | 0.05 degree | 0.01 degree | 0.01 degree |
| Frequency of detection |  |  |  |  |  |  |
| Running speed 50 km/h | 7 time/second | 55 time/second | 55 time/second | 55 time/second | 55 time/second | 220 time/second |
| Running speed 20 km/h | 2.8 time/second | 22 time/second | 22 time/second | 22 time/second | 22 time/second | 89 time/second |
| Resolving power of longitudinal force detection <N> | About 7500 | About 7500 | About 750 | About 380 | About 75 | About 75 |
| Effectiveness to vehicle control system | X | X | Δ | ○ | ◉ | ◉ |

As shown in FIGS. 6(A) and 6(B), it is possible to detect the data of the longitudinal force similar to the actual measurement value by using the detecting method and apparatus in accordance with the present invention. Further, as shown in Table 1, it is necessary to make the resolving power of the second sensor (the angle sensor) not more than 0.1 degree, in order to effectively utilize the detection data for the vehicle control system.

What is claimed is:

1. A method of detecting a longitudinal force of a tire which detects the longitudinal force in a circumferential direction applied to the tire, comprising:

at least one mark provided in the tire on one circumferential line around a tire axis;

a first sensor fixed to a vehicle body and capable of sequentially detecting a passage of said mark rotating together with the tire;

a second sensor capable of detecting a rotation angle θ of an axle; and a computing means for computing a longitudinal force applied to the tire on the basis of an information from said first and second sensors, wherein said computing means comprises:

(1) storing an information of a rotation angle θr of the axle detected by said second sensor when receiving information of the passage signal from said first sensor according to the passage of said mark;

(2) previously storing an information of a no-load rotation angle θo of the axle detected by said second sensor when receiving information of the passage signal from said first sensor according to the passage of said mark, as the tire rotates in a no-load state;

(3) computing a tire warp angle αr corresponding to a difference (θo−θr) between said rotation angle θr and said no-load rotation angle θo; and (4) computing a longitudinal force Fr of a tire applied during the running from said warp angle αr using a a previously determined relational equation between the tire warp angle α and the longitudinal force F applied to the tire.

2. A method of detecting a longitudinal force of a tire as claimed in claim 1, wherein a resolving power of said second sensor is set to be not more than 0.10 degree.

3. A method of detecting a longitudinal force of a tire as claimed in claim 1, wherein said circumferential line is arranged in a side wall portion of the tire, and 4 to 72 said marks are provided on the circumferential line.

4. An apparatus for detecting a longitudinal force of a tire which detects the longitudinal force in a circumferential direction applied to the tire, comprising:

at least one mark provided in the tire on one circumferential line around a tire axis;

a first sensor fixed to a vehicle body and capable of sequentially detecting a passage of said mark rotating together with the tire;

a second sensor capable of detecting a rotation angle θ of an axle; and a computing means for computing a longitudinal force applied to the tire on the basis of an information from said first and second sensors, wherein said computing means comprises:

a rotation angle information memory portion sequentially storing an information of a rotation angle θr of the axle detected by said second sensor when receiving the information of the passage signal from said first sensor according to the passage of said mark;

a no-load rotation angle information memory portion previously storing an information of a no-load rotation angle θo of the axle detected by said second sensor when receiving the information of the passage signal from said first sensor according to the passage of said mark as the tire rotates in a no-load state;

a first computing portion sequentially computing a tire warp angle αr corresponding to a difference (θo−θr) between the rotation angle θr of said rotation angle information memory portion and the no-load rotation angle θo of said no-load rotation angle information memory portion; and a second computing portion sequentially computing a longitudinal force Fr of a tire applied during the running from said warp angle αr computed by said first computing portion, using a previously determined relational equation between the warp angle α and the longitudinal force F applied to the tire.

5. An apparatus for detecting a longitudinal force of a tire as claimed in claim 4, wherein a resolving power of said second sensor is set to be not more than 0.10 degree.

6. An apparatus for detecting a longitudinal force of a tire as claimed in claim 4, wherein said second sensor is used as a sensor of a rotation speed for an ABS, or a sensor of a rotation acceleration.

7. An apparatus for detecting a longitudinal force of a tire as claimed in claim 4, wherein said mark is provided in a side wall portion of the tire.

8. An apparatus for detecting a longitudinal force of a tire as claimed in claim 7, wherein said mark is provided in a region in an outer side in a radial direction from a tire maximum width position.

9. An apparatus for detecting a longitudinal force of a tire as claimed in claim 4, wherein 4 to 72 said marks are provided on the circumferential line at an equal interval.

10. An apparatus for detecting a longitudinal force of a tire as claimed in claim 4, wherein said computing means computes a direction of the longitudinal force F according to positive or negative of the difference (θo−θr) between said rotation angle θr and said no-load rotation angle θo.

* * * * *